(12) United States Patent
Kitchener et al.

(10) Patent No.: US 8,797,050 B2
(45) Date of Patent: Aug. 5, 2014

(54) IEC 61158-2 ELECTRICAL CIRCUIT WITH WATER DETECTION MEANS COMPRISING A PHYSICAL LAYER ATTRIBUTE MODIFIER

(75) Inventors: Renato Kitchener, West Sussex (GB); Gunther Rogoll, Mannheim (DE)

(73) Assignee: Pepperl + Fuchs GmbH (DE)

( * ) Notice: Subject to any disclaimer, the term of this patent is extended or adjusted under 35 U.S.C. 154(b) by 171 days.

(21) Appl. No.: 13/383,692

(22) PCT Filed: Jul. 14, 2010

(86) PCT No.: PCT/GB2010/001347
§ 371 (c)(1),
(2), (4) Date: Jan. 12, 2012

(87) PCT Pub. No.: WO2011/007142
PCT Pub. Date: Jan. 20, 2011

(65) Prior Publication Data
US 2012/0118047 A1    May 17, 2012

(30) Foreign Application Priority Data
Jul. 17, 2009   (GB) .................................. 0912444.7

(51) Int. Cl.
*G01R 27/08*   (2006.01)
*G01M 3/16*    (2006.01)
*G08B 21/00*   (2006.01)
*G01M 3/04*    (2006.01)
*G01N 33/18*   (2006.01)
*G01N 27/06*   (2006.01)
*A61M 5/168*   (2006.01)
*B67D 3/00*    (2006.01)
*G01N 27/04*   (2006.01)

(52) U.S. Cl.
CPC ................ *G01M 3/16* (2013.01); *G01M 3/045* (2013.01); *G01N 33/1886* (2013.01); *A61M 5/16831* (2013.01); *B67D 3/00* (2013.01); *G01N 27/06* (2013.01); *G01N 27/048* (2013.01)
USPC ......... 324/694; 324/693; 73/40.5 R; 340/605; 340/620

(58) Field of Classification Search
CPC ......... G01M 3/16; G01M 3/045; G01M 3/00; G01N 27/06; G01N 33/1886; A61M 5/16831
See application file for complete search history.

(56) References Cited

U.S. PATENT DOCUMENTS 5,272,467 A * 12/1993 Krauleidies ................... 340/604
7,019,541 B2 * 3/2006 Kittrell ......................... 324/696

(Continued)

FOREIGN PATENT DOCUMENTS

| GB | 2377995 A | 1/2003 |
| WO | 2009/063213 A1 | 5/2009 |
| WO | 2009/068879 A1 | 6/2009 |

OTHER PUBLICATIONS

International Search Report and Written Opinion, PCT/GB2010/001347, dated Sep. 20, 2010.

(Continued)

*Primary Examiner* — Jermele M Hollington
(74) *Attorney, Agent, or Firm* — Lerner, David, Littenberg, Krumholz & Mentlik, LLP

(57) ABSTRACT

An electrical circuit confirming to the IEC 61158-2 standard comprising a power supply, a device as a load thereof, and monitoring means adapted to monitor one or more physical layer attributes of the electrical circuit, in which the device comprises an enclosure, device function electronics disposed therein and two terminals connecting said device function electronics to said electrical circuit, in which water detection means is disposed inside said enclosure, and comprises water detection probes and a physical layer attribute modifier mounted across said electrical circuit in parallel with said device function electronics, and in which when said water detection probes detect water said physical layer attribute modifier makes a modification to a physical layer attribute of the electrical circuit, which modification is detectable by said monitoring means.

19 Claims, 3 Drawing Sheets

(56) References Cited

U.S. PATENT DOCUMENTS

| | | | |
|---|---|---|---|
| 7,521,944 B2* | 4/2009 | Wehrs | 324/694 |
| 2005/0253601 A1* | 11/2005 | Kittrell | 324/696 |
| 2008/0156090 A1 | 7/2008 | Wehrs | |

OTHER PUBLICATIONS

Gunther Rogall et al: "Advanced Online Physical Layer Diagnostics" Technical White Paper Pep Perl + Fuchs, XX, XX, Aug. 30, 2006, page Complete, XP002434472.

* cited by examiner

Figure 1    *PRIOR ART*
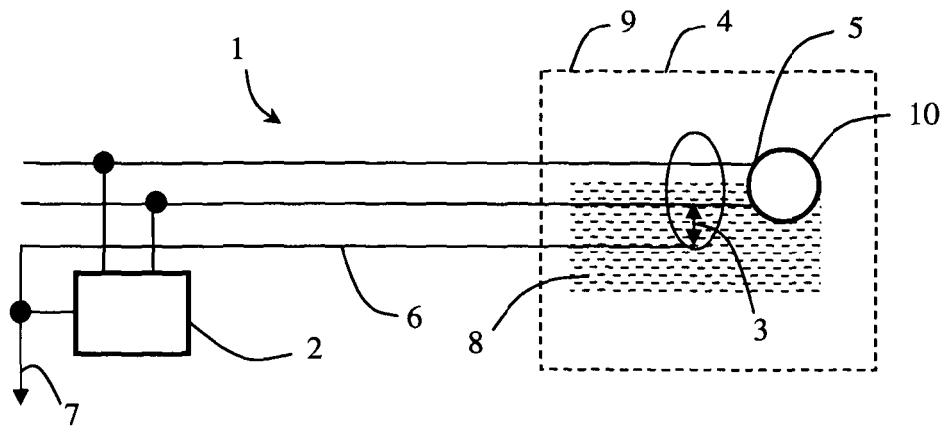
Figure 2    *PRIOR ART*
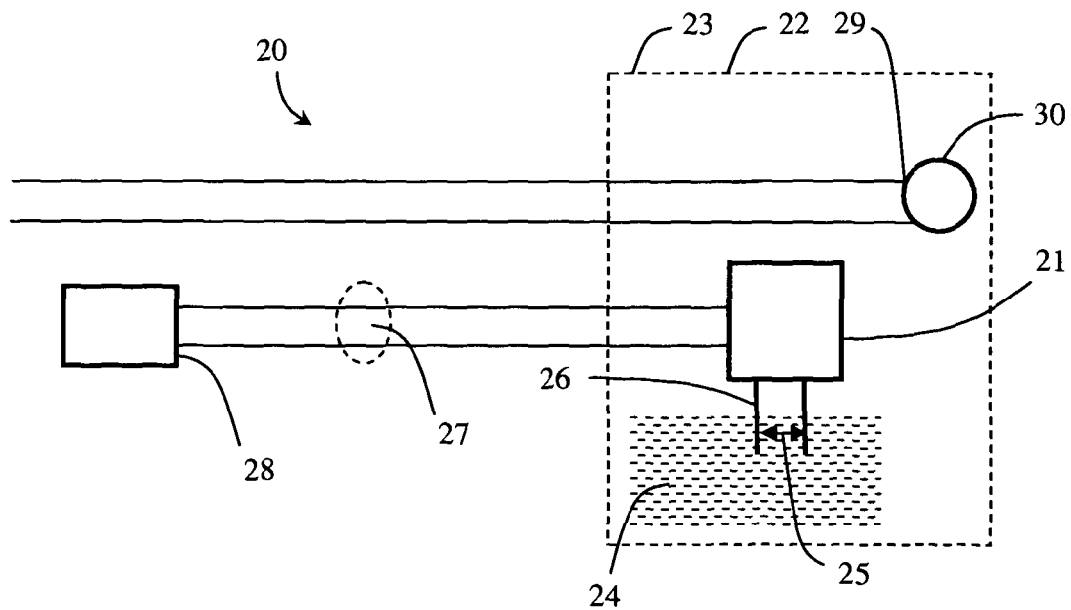

IEC 61158-2 ELECTRICAL CIRCUIT WITH WATER DETECTION MEANS COMPRISING A PHYSICAL LAYER ATTRIBUTE MODIFIER

CROSS-REFERENCE TO RELATED APPLICATIONS

The present application is a national phase entry under 35 U.S.C. §371 of International Application No. PCT/GB2010/001347 filed Jul. 14, 2010, published in English, which claims priority from Great Britain Patent Application No. 0912444.7 filed Jul. 17, 2009, all of which are incorporated herein by reference.

BACKGROUND OF THE INVENTION

This invention relates to an electrical circuit conforming to the IEC 61158-2 standard with water detection means comprising a physical layer attribute modifier, for use in detecting the ingress of water into field devices in an Intrinsically Safe area.

Fieldbus (or field bus) is the name of a family of industrial computer network protocols used for real-time distributed control, now standardized as IEC 61158. A complex automated industrial system, for example a fuel refinery, usually needs an organized hierarchy of controller systems to function. In this hierarchy there is a Human Machine Interface (HMI) at the top, where an operator can monitor or operate the system. This is typically linked to a middle layer of programmable logic controllers (PLC) via a non time critical communications system (e.g. Ethernet). At the bottom of the control chain is the fieldbus, which links the PLCs to the components which actually do the work such as sensors, actuators, electric motors, console lights, switches, valves and contactors.

Fieldbus is often used in Intrinsically Safe environments, for example combustible atmospheres, and in particular gas group classification IIC, Hydrogen and Acetylene, and below, for example gas group IIB and IIA, for gas and/or dust. Using the Fieldbus protocol, field instruments and equipment in such an environment are controlled and monitored remotely via an electrical communications circuit often provided in the same electrical circuit as the power to drive the field instruments.

Fieldbus physical layer diagnostics for IEC 61158 type networks has been introduced successfully to the mainstream processing industry in the last few years. The physical layer specifications are standardised as IEC 61158-2. In a typical electrical communications circuit there is a power supply, an Intrinsic Safety barrier of some kind, a trunk section leading out into the field, and one or more devices, or device couplers with spur sections connected thereto, as the load thereof. The devices send data signals in use to a control system, usually mounted in a non Intrinsically Safe area at the power supply end of the circuit. A diagnostic module is also mounted in the electrical circuit, usually at the same location as the control system, and it works by measuring physical layer attributes of the electrical circuit and the network hardware, and in part, the physical software or protocol being used.

Changes in IEC61158-2 loads and/or physical layer attributes can often lead to a segment failure, and the diagnostic module is set up to detect such changes so that remedial action can be taken.

Water ingress into field devices is one fault that must be detected in order to prevent corrosion of the electrical terminals or cables inside the field device by electrolytic erosion, which can eventually lead to device failures. In extreme cases submersion of the signal lines or terminals in water or other conductive fluids can lead to swift full signal or segment failures.

In any event, instruments in outdoor hazardous areas must be protected to a minimum of IP54 in accordance with the EN60529 standard, and water ingress represents a breach of this. In addition, condensing water vapour inside the instrument enclosure usually infringes the humidity requirements of the instrument, as most specifications allow only 95% relative non-condensing humidity.

Typically, field instruments (devices) have terminal and electronic enclosures. The outer terminal enclosures comprise a small volume, 'O' ring sealed enclosures with at least 1 cable gland entry, typically 2 with one blanked off. The electronic enclosures have no cable entry or a need to remove the cover on site, so the likelihood of water ingress is far lower. They are often fitted with potted electronics and/or have 'O' ring seals with long threaded covers, and are often able to meet ratings of IP66 to IP68. Unfortunately ingress of water into the terminal enclosures is a common occurrence in practice.

For every segment of the system, there are typically up to 16 instruments. This means that the probability of the terminal enclosure of at least one instrument on a segment filling with water is very high in comparison to the device coupler housing. These need less maintenance and have a larger enclosure volumes with drain facilities.

One known way to detect water ingress in a field device is to detect a ground fault using an earth leakage detection system, and such an arrangement is shown in FIG. 1. In this arrangement an electrical circuit 1 comprises an earth leakage detection system 2, which detects conductivity 3 in a device 4 between the terminals/poles 5 and the shield 6, and therefore the ground 7, through conductive liquid 8. This takes place inside the device enclosure 9, adjacent to the device electronics 10.

Measuring for an earth fault is advantageous over measuring for a differential change because it is discernable over load changes. A load change and the effects of water bridging signal poles 5 would cause similar differential changes in the circuit 1, so a purely differential measurement would not be reliable.

However, these systems have a number of drawbacks. First of all, they can only detect the presence of high conductivity water. Cable length and voltage restrictions to meet the requirements of Intrinsic Safety make the detection of purer water impossible. The applicant, as well as other companies like MTL (Cooper Crouse-Hinds Co) produce such systems, and as an example the MTL 4220 product can only detect conductivity equivalents of 10 kOhm or less, whereas measurements of 250 kOhms to 1 MOhm and higher are typical for clean rain water and precipitation at low excitation detection voltages.

Even complete immersion of the terminals 5 in condensate or rain water with a very low conductivity will not lead to a normally measurable current or impedance change. However such an event will start the process of galvanic corrosion which can cause a failure. Bench testing has shown a low concentration saline solution will dissolve (by galvanic corrosion of the anode) the signal wires within a matter of minutes. Dissolved metal trace elements leaking form the terminals and wire can quickly increase the conductivity of the water so it can be detected, but by then failure can occur before any evasive action can be taken.

The second main problem is that even if the water is conductive enough to be detected straight away, the poles 5 are already submerged when detection is made. Submersion can rapidly lead to damage and signal problems, often before remedial action can be taken. An earth leakage detection system like that shown in FIG. 1 relies on the electrolytic affect between the terminals 5 and the shield 6 or ground 7, and at this point the damage is already in progress. If the conductivity equivalent is 10 kOhms or less, the acceleration in conductivity due to localised metals dissolving into the solution can quickly result in an over current situation, and too rapidly to allow for proactive maintenance. In other words, the principal of monitoring for the submergence of terminals is a flawed one in any event, because damage in some cases may be unpreventable.

Another drawback with earth leakage detection systems like that shown in FIG. 1 is that they are autonomous systems that comprise hardware and cabling for sensing, alarm and power, which is additional to the existing electrical circuit 1. This adds costs and increases the likelihood of failures. The power supply must also be rendered Intrinsically Safe.

A further drawback with earth leakage detection systems is that they rely on connection to the shield 6, which often does not extend inside the field device 4, or is not present in a suitable position for connection.

An alternative known way to detect water ingress in a field device is to use an autonomous sensor inside the field device which can detect the presence of water, and such an arrangement is shown in FIG. 2. In this arrangement an electrical circuit 20 comprises an autonomous detector and transmitter 21 disposed inside the terminal enclosure 22 of the field device 23, which detects the onset of water ingress 24 by sensing conductivity 25 with detector probes 26. An alarm is sent through separate power and signal lines 27 to a diagnostic and alarm module 28.

Because this system is autonomous it can be adapted to detect high purity low conductivity water, and by positioning the probes 26 away from the terminals/poles 29 in the field device 23 it can do so long before any damage is caused to the terminals/poles 29 or the device electronics 30. There is also no requirement for any connection to the shield. Therefore, this arrangement has distinct advantages over the earth leakage detection system shown in FIG. 1.

However, there are still a number of major drawbacks. Firstly, given the number of field devices used in practice on site, it is very complex and very costly to install such autonomous systems in each and every field device.

In addition, this solution still requires hardware, electronics, cabling and a power supply additional to the existing infrastructure, all of which must be rendered Intrinsically Safe, which requires calculations for all parameters and additional wiring diagrams, which all adds to the costs.

This additional equipment increases the likelihood of failure generally. In addition, each field device will need an additional cable gland, which actually increases the likelihood of water ingress.

Therefore, a solution is required which can detect low conductivity water ingress in a field device, detect water ingress before any terminal in the field device is wetted, and relay that information to maintenance crews without the need for additional wiring or a wireless link, and via long trunk cables and any isolated device couplers. This eliminates the requirement for any additional power or other wiring, other than simple connection to a bus (including a shield if required). In order to be practical the solution must also meet the requirements of the Intrinsic Safety (EEx ia or ib) "simple apparatus" definition, and have connection means suitable for Intrinsically Safe wiring practice. Some field device terminal enclosures are very small in area and/or in volume, so any solution must also be small and simple. Finally the solution must maintain the integrity of the Fieldbus signal.

It would be theoretically possible to achieve many of the above goals by making water detection a function of the field device. In other words, the field device electronics can include a water detection function, and the field device electronics can communicate the detection of water to the control system via its Fieldbus telegram. However, such an arrangement would be self-defeating because it would essentially comprise an entire Fieldbus field device installation on its own. In addition, integrating such a function into hundreds of different Fieldbus device types would be very costly from a design and manufacturing point of view, and not all manufacturers would be willing to integrate such systems into every model type. In addition, the function would consume part of the Fieldbus telegram, limiting the communication potential of the primary function of the device.

SUMMARY OF THE INVENTION

Therefore, according to the present invention, an electrical circuit confirming to the IEC 61158-2 standard comprises a power supply, a device as a load thereof, and monitoring means adapted to monitor one or more physical layer attributes of the electrical circuit, in which the device comprises an enclosure, device function electronics disposed therein and two terminals connecting said device function electronics to said electrical circuit, in which water detection means is disposed inside said enclosure, and comprises water detection probes and a physical layer attribute modifier mounted across said electrical circuit in parallel with said device function electronics, and in which when said water detection probes detect water said physical layer attribute modifier makes a modification to a physical layer attribute of the electrical circuit, which modification is detectable by said monitoring means.

Thus, the present invention involves detecting the ingress of water into the enclosure of a field device in a way which is essentially autonomous of the circuit, but communicating such detection in an integrated way with a deliberate modification of any physical layer attribute of the circuit which can be detected by the monitoring means. The modification can have no communicative meaning as such, but a control system connected to the monitoring means can be adapted to interpret the modification, and decipher its meaning.

The key advantage of the present invention is that the communication of the detection of water ingress is conducted using the existing electrical circuit and its physical layer monitoring means. There is therefore no need for extra Intrinsically Safe cabling, power, electronics or cable glands. Further, as the water detection means are basically autonomous, they can be adapted to detect high purity low conductivity water that an earth leakage detection system cannot. By positioning the water detection probes away from the terminals in the field device detection can also be made long before any damage is caused. There is also no requirement for any connection to the shield.

In a preferred constriction said device can have a normal operating orientation in which said water detection probes can be physically disposed below said terminals connecting said device function electronics to said electrical circuit. Therefore, the collection of water at the bottom of the enclosure can be detected before the terminals are under any real threat of immersion.

The monitoring means can be any of the known physical layer diagnostic systems (PLDS) which monitor trunk or spur currents and are able to monitor the bus signal level and noise influence. These levels are much higher than the effect that low conductivity water would have on the bus or spur, so known arrangements are not able to detect water ingress in a field device on their own, in particular because they also usually have a noise floor. For example, medium purity rain water has an approximate DC resistance of 20 kOhms to 1 MOhm, and at 9V this gives a current of between 9 uA and 450 uA. Therefore, a resolution of 0.0025% for a 350 mA full scale measurement of current would be required, and in addition there would need to be signal measurement lower than the noise floor. However, the present invention involves a modification to the electrical circuit which can be specifically adapted to be readily detectable by a PLDS. Advantageously, it is possible to make such a modification which does not disrupt the Fieldbus telegrams.

Therefore, in a preferred construction, the electrical circuit can comprise an electrical power and communications circuit, and the device can be adapted to send and receive data signals over the electrical circuit. Preferably the modification to a physical layer attribute of the electrical circuit may not interfere with said data signals.

In one version of the invention said modification to a physical layer attribute of the electrical circuit can comprise an intermediate unbalance from pole to shield of said electrical circuit, i.e. 3 kOhm from pole to shield. However, this configuration would require a shield/earth connection and a third wire.

Alternatively, said modification to a physical layer attribute of the electrical circuit can comprise a constant current in the electrical circuit with a high c.c. sink impedance.

Alternatively, said modification to a physical layer attribute of the electrical circuit can comprise ramping up and down the current of the electrical circuit. This can be done to, say 10 mA c.c., at a rate of not more than +/−1 mA/ms.

Alternatively, said modification to a physical layer attribute of the electrical circuit can comprise the introduction of a common mode signal, detectable by the unbalance measurement in the PLDS.

Alternatively, said modification to a physical layer attribute of the electrical circuit can comprise an attenuation of the data signal level, either constantly or intermittently.

Which ever modification is employed, it can be variable or binary over time, for example a pulsed 5 mA signal at a frequency of 0.1 Hz with equal mark-space.

As a shield connection is rarely present within a field instrument due to the requirement to prevent multiple grounding points in Intrinsically Safe systems, the preferred options would be a constant current in the electrical circuit with a high c.c. sink impedance, or a ramping up the current, with a possibility of using an attenuation of the data signal level for isolated couplers with repeaters.

It will be appreciated that all of the above modification options are differential in nature, so they will work in a system with a differential wiring pair for signal and power, and within the physical layer attribute envelope.

Preferably said water detection means can be powered by the electrical circuit. This is very simple to achieve and prevents the need for any additional Intrinsically Safe power supplies.

In one version of the invention the device can be a field instrument, and said device function electronics can comprise instrumentation electronics. Alternatively, said device can be a device coupler, and said device function electronics can comprise coupling electronics adapted to connect to further devices or spurs.

In one version of the invention an electrolyte, such as salt, can be provided inside the enclosure. This would allow a higher conductivity to be established. The electrolyte can be provided on the water detection probes.

As referred to above, the invention is preferably used with an Intrinsically Safe two wire Fieldbus (IEC 61158) circuit.

BRIEF DESCRIPTION OF THE DRAWINGS

The invention can be performed in various ways, but one embodiment will now be described by way of example, and with reference to the accompanying drawings, in which:

FIG. 1 is a diagrammatic view of a first prior art electrical circuit comprising a water ingress detection system;

FIG. 2 is a diagrammatic view of a second prior art electrical circuit comprising a water ingress detection system;

DESCRIPTION

Figure 3:
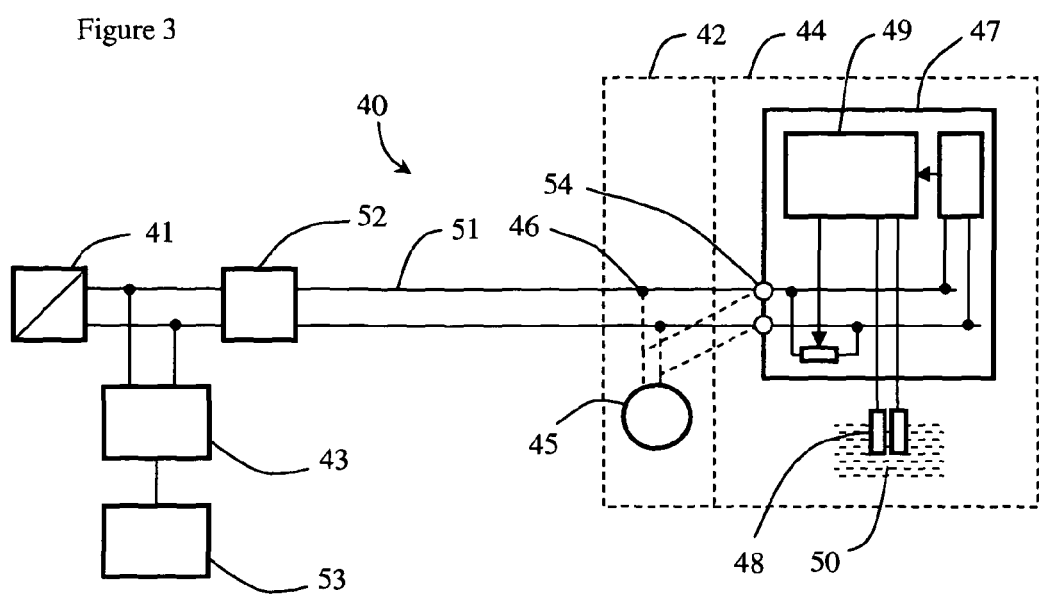
FIG. 3 is a diagrammatic view of an electrical circuit comprising a water ingress detection system according to the present invention.

As shown in FIG. 3, an electrical circuit 40 confirming to the IEC 61158-2 standard comprises a Fieldbus power supply 41, a device 42 as a load thereof, and monitoring means adapted to monitor one or more physical layer attributes of the electrical circuit 40, in the form of physical layer attribute diagnostic module 43. The device 42 comprises an enclosure 44, device function electronics 45 disposed therein, and two terminals 46 connecting said device function electronics 45 to said electrical circuit 40. Water detection means 47 is disposed inside said enclosure 44, and comprises water detection probes 48 and a physical layer attribute modifier 49 mounted across said electrical circuit 40 in parallel with said device function electronics 45. When said water detection probes 48 detect water 50, said physical layer attribute modifier 49 makes a modification to a physical layer attribute of the electrical circuit 40, which modification is detectable by said monitoring means (43).

The electrical circuit 40 is an Intrinsically Safe Fieldbus (IEC 61158) circuit, in which the trunk section 51 reaching out into the field is rendered Intrinsically Safe by intrinsic safety means 52, which can be any of the known systems. The physical layer attribute diagnostic module 43 is shown mounted outside of the Intrinsically Safe area, and it connected to a general control and monitoring system 53, which would usually be in a control room. The control and monitoring system 53 communicates via the Fieldbus protocol with the field device electronics 45, which can comprise any conventional function.

The physical layer attribute modifier 49 is two wire powered, and takes its power from the same point as the device electronics 45. It will be appreciated that for this system to work on a trunk or spur, the input impedance 54, must be high at all times. The probes 48 are positioned inside the enclosure 44 below the terminals 46 and the device electronics 45, such that gravity leveled ingress will make contact with the probes 48 before anything else inside the enclosure 44.

On detection of conductivity between the probes 48, the physical layer attribute modifier 49 makes a modification to a physical layer attribute of the electrical circuit 40, which is readily detectable by the physical layer attribute diagnostic module 43. This is communicated to the control system 53 and remedial action can be taken.

As referred to above, there are many different modifications which can be made, and the physical later attribute modifier 49 can be adapted to perform any of them, as required. The modification can be to any physical layer attribute which is measurable, for example an unbalance (requiring a shield/earth connection and a third wire), or a variable or binary modification over time, for example pulsed 5 mA signals at a frequency of 0.1 Hz with equal mark-space. Further, a constant current with a high c.c. sink impedance can be applied, the current can be ramped up and down, a common mode signal can be introduced, or the data signal level can be constantly or intermittently attenuated.

Figure 4:
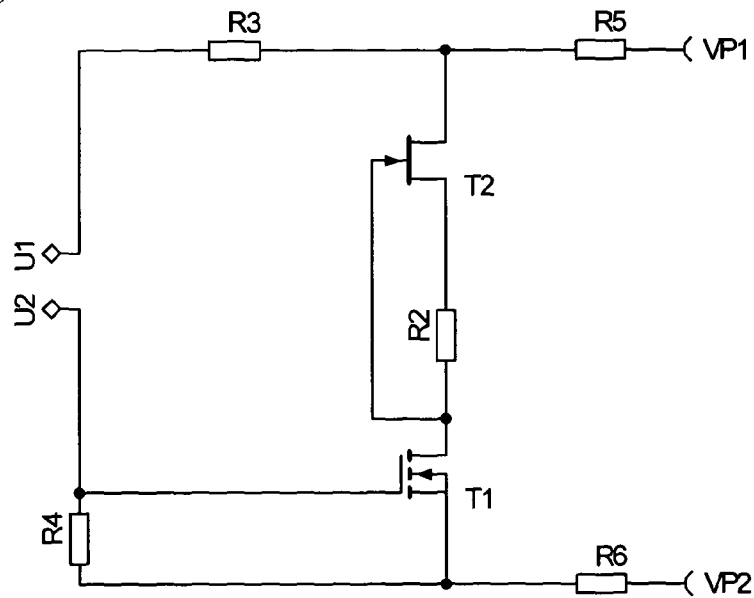
FIG. 4 is a circuit diagram of a part of the electrical circuit as shown in FIG. 3; and, FIG. 5 is a front view of a part of the electrical circuit as shown in FIG. 3.

FIG. 4 illustrates a very rudimentary Intrinsically Safe 'simple apparatus' solution that can operate as the water detection means 47. Upon detection of water ingress by the probes 48, the spur/trunk current is increased by introducing a constant current sink. It will be appreciated that this is advantageous because it does not effect any other parameter such as signal levels. There are also no capacitors or inductors in this simple circuit, and it can therefore be classed as 'simple apparatus' for Zone 0 and Zone 1 Intrinsically Safe purposes, as well as for any other Zone certification or equivalents. This is advantageous because manufacturer certified "simple apparatus" for use with a given power source can be placed on any Intrinsically Safe circuit without the need for system certification, making it suitable for use within the terminal enclosure of pre-certified instruments.

Figure 5:
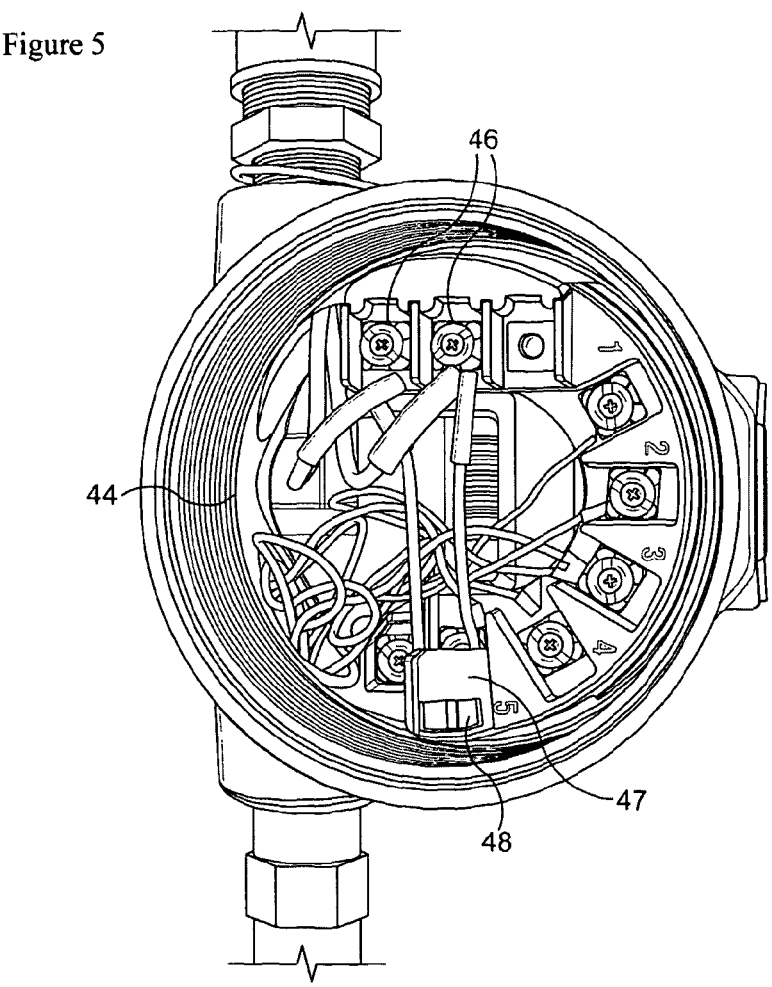

FIG. 5 shows physically how the device enclosure 44 can be configured, with the terminals 46 at the top, and with the water detection means 47 and its probes 48 positioned at the lowest point in the enclosure 44.

For a more defined warning of condensation or ultrahigh purity water ingress, salts, or other electrolytes, can be added to the surfaces or undersides of the probes 48, or elsewhere in the enclosure 44, which would give the water a higher conductivity. In practice this would not normally be required because ultra high purity water would actually not cause a failure. If metal leaching occurs as a result of such ingress it is most likely to occur at the probes 48 first given their position, and if so they can perform a sacrificial function to cause the triggering of the modification and subsequent alarm.

The embodiment shown in FIGS. 3 to 5 can be altered without departing from the scope of claim 1. For example, in one alternative embodiment (not shown) the device is a coupler rather than an instrument, and the electronics therein comprises coupling electronics adapted to connect to further devices or spurs.

Therefore, a water ingress detection system is provided which has all the above described advantages that known autonomous detection systems have over earth leakage detection systems, but none of the drawbacks of extra cabling, electronics and power. By utilising changeable physical layer attributes of the existing circuit, a warning can be communicated to the control room via the existing physical layer attribute diagnostic module. This can be achieved using "simple apparatus" in a cost-effective way.

The invention claimed is:

1. An electrical circuit confirming to the IEC 61158-2 standard comprising a power supply, a device as a load thereof, a trunk section and monitoring means monitoring one or more physical layer attributes of the electrical circuit,
   in which the device comprises an enclosure, and device function electronics disposed therein, in which said device function electronics are connected to said trunk section by two terminals,
   in which water detection means is disposed inside said enclosure, and comprises water detection probes and a physical layer attribute modifier mounted to said trunk section in parallel with said device function electronics,
   in which said water detection probes are physically separate from said two terminals,
   and in which when said water detection probes detect water inside said enclosure said physical layer attribute modifier communicates such detection by making a deliberate predetermined modification to a physical layer attribute of the electrical circuit, which modification is separate from any physical layer attribute change caused by water being present in said device function electronics or between said two terminals, and which modification is detectable and decipherable by said monitoring means.

2. An electrical circuit as claimed in claim 1 in which said device has a normal operating orientation in which said water detection probes are physically disposed below said terminals connecting said device function electronics to said trunk section.

3. An electrical circuit as claimed in claim 1 in which the electrical circuit comprises an electrical power and communications circuit, in which the device is adapted to send and receive data signals over the electrical circuit, and in which said modification to a physical layer attribute of the electrical circuit does not interfere with said data signals.

4. An electrical circuit as claimed in claim 3 in which said modification to a physical layer attribute of the electrical circuit comprises an intermediate unbalance from pole to shield of said electrical circuit.

5. An electrical circuit as claimed in claim 3 in which said modification to a physical layer attribute of the electrical circuit comprises a constant current in the electrical circuit with a high c.c. sink impedance.

6. An electrical circuit as claimed in claim 3 in which said modification to a physical layer attribute of the electrical circuit comprises ramping up and down the current of the electrical circuit.

7. An electrical circuit as claimed in claim 3 in which said modification to a physical layer attribute of the electrical circuit comprises the introduction of a common mode signal.

8. An electrical circuit as claimed in claim 3 in which said modification to a physical layer attribute of the electrical circuit comprises an attenuation of the data signal level, either constantly or intermittently.

9. An electrical circuit as claimed in claim 4 in which said modification is varied over time.

10. An electrical circuit as claimed in claim 1 in which said water detection means is powered by the electrical circuit.

11. An electrical circuit as claimed in claim 1 in which said device is a field instrument and said device function electronics comprises instrumentation electronics.

12. An electrical circuit as claimed in claim 1 in which said device is a device coupler, and in which said device function electronics comprises coupling electronics adapted to connect to further devices or spurs.

13. An electrical circuit as claimed in claim 1 in which an electrolyte is provided inside the enclosure.

14. An electrical circuit as claimed in claim 12 in which said electrolyte is provided on the water detection probes.

15. An electrical circuit as claimed in claim 1 in which the electrical circuit is an Intrinsically Safe two-wire Fieldbus electrical circuit.

16. An electrical circuit as claimed in claim 5 in which said modification is varied over time.

17. An electrical circuit as claimed in claim 6 in which said modification is varied over time.

18. An electrical circuit as claimed in claim 7 in which said modification is varied over time.

19. An electrical circuit as claimed in claim 8 in which said modification is varied over time.

* * * * *